United States Patent
Fauran et al.

[11] 4,025,514
[45] May 24, 1977

[54] ARYLAMINO PYRIMIDINIC DERIVATIVES

[75] Inventors: Claude P. Fauran, Paris; Guy R. Bourgery, Colombes; Guy M. Raynaud, Paris; Claude J. Gouret, Meudon, all of France

[73] Assignee: Delalande S.A., Courbevoie, France

[22] Filed: Aug. 16, 1976

[21] Appl. No.: 714,472

Related U.S. Application Data
[63] Continuation-in-part of Ser. No. 502,285, Sept. 3, 1974, Pat. No. 3,978,055.

[30] Foreign Application Priority Data

Sept. 20, 1973 France .......................... 73.33831
Mar. 26, 1974 France .......................... 74.10327

[52] U.S. Cl. .......................... 260/256.4 N
[51] Int. Cl.² .......................... C07D 239/42
[58] Field of Search .......................... 260/256.4 N

[56] References Cited
UNITED STATES PATENTS

| | | | |
|---|---|---|---|
| 3,321,478 | 5/1967 | English et al. | 260/256.4 N |
| 3,816,423 | 6/1974 | Kim et al. | 260/256.4 N |

*Primary Examiner*—Paul M. Coughlan, Jr.
*Attorney, Agent, or Firm*—Woodhams, Blanchard and Flynn

[57] ABSTRACT

Compounds of the formula

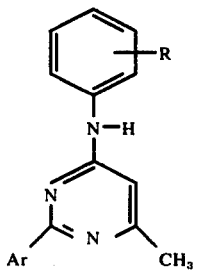

wherein Ar is phenyl or phenyl substituted by one or more halogens, a trifluoromethyl, a methylenedioxy, one or more methoxy, an alkyl having one to 4 carbon atoms or a dimethylamino,
and R is

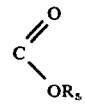

and $R_5$ is alkyl of 1 to 4 carbon atoms, 2,3-dihydroxypropyl or 2,2-dimethyl dioxolan-4-yl methyl or hydroxycarbonylmethyl.

The compounds are obtained by reacting 2-Ar-4-chloro-6-methyl pyrimidine, with

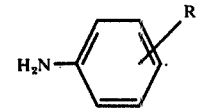

The compounds possess sedative, antiinflammatory, antiulcerous, and anti-anoxemia properties.

3 Claims, No Drawings

ARYLAMINO PYRIMIDINIC DERIVATIVES

CROSS REFERENCE TO RELATED APPLICATION

This application is a continuation-in-part of Ser. No. 502,285, filed Sept. 3, 1974, U.S. Pat. No. 3,978,055.

This invention relates to arylamino pyrimidine derivatives.

According to the invention, there are provided compounds having the formula (I)

wherein
1. Ar is m-fluorophenyl and R is ethyl, or
2. Ar is 3,4,5-trimethoxyphenyl and R is 2,2-dimethyl-1,3-dioxolan-4-yl methyl.

The process according to the invention consists in condensing in acetic acid and in the presence of hydrochloric acid, a 2-aryl-4-chloro-6-methyl pyrimidine of the general formula:

(II)

in which:
-Ar is as defined above, with an anilino derivative of the general formula:

(III)

in which R' is an alkoxycarbonyl group of formula in which R is ethyl, or to obtain a compound of the formula:

(IV)

or in R' is a methoxycarbonyl group, followed by a transesterification process in the presence of sodium with 2,2-dimethyl-4-hydroxymethyl-1,3-dioxolane to produce a compound of the formula:

(V)

The following preparation is given by way of example to illustrate the invention.

EXAMPLE 1

N-[2-3',4',5'-trimethoxyphenyl)-6-methyl-4-pyrimidyl] (2'',2''-dimethyl-1'',3''-dioxolan-4''-yl) methyl anthramilate.

(Code No. 71510)

1st step: N-[2-(3',4',5'-trimethoxy phenyl)-6 methyl-4 pyrimidyl] methyl anthramilate Code No. 72479

A mixture of 39.8g of 2-(3',4',5'-trimethoxy phenyl)-4-chloro-6-methyl pyrimidine and 20.4g of anthranilic acid methyl ester in 270 cc of acetic acid in the presence of 0.9 cc of concentrated hydrochloric acid is heated at 90° C for 60 minutes. After cooling, the solution is diluted with 2 l of water and alkanized with ammonia.

The precipitate formed is filtered, washed with water and recrystallized from ethanol.

Melting point = 121° C
Yield = 56%
Empirical formula = $C_{22}H_{23}N_3O_5$
Molecular weight = 409.43
Elementary analysis:

| Elementary analysis: | | | |
|---|---|---|---|
| | C | H | N |
| Calculated % | 64.53 | 5.66 | 10.26 |
| Found % | 64.74 | 5.85 | 10.31 |

2nd step:
N-[2-(3',4',5'-trimethoxyphenyl)-6-methyl-4-pyrimidyl] (2'',2''-dimethoxy-1'',3''-dioxolan-4''-yl) methyl anthranilate.

Code No. 71510

0.1g of sodium is dissolved in 80 cc of 2,2-dimethyl-4-hydroxymethyl-1,3-dioxolane. To this solution are added 27.5g (0.067 mole) of N-[2-(3',4',5'-trimethoxy phenyl)-6 methyl-4-pyrimidyl]methyl anthranilate, obtained by the procedure described in the preceding step.

The mixture is heated for 5 hours at 145° C, the methanol formed during the course of the reaction being distilled off. After cooling, the solution obtained is diluted with 3 liters of water.

The precipitate formed is filtered, washed with water and recrystallized from ethanol.

Melting point = 118° C
Yield = 56%
Empirical formula = $C_{27}H_{31}N_3O$
Molecular weight = 509.54

| Elementary analysis : | | | |
|---|---|---|---|
| | C | H | N |
| Calculated % | 63.64 | 6.13 | 8.25 |
| Found % | 64.84 | 6.02 | 8.34 |

The derivatives listed in the following Table I have been prepared by the same mode of operation.

As examples, table II below gives, for a certain number of derivatives, the first dose providing significant protection by intraperitoneal injection.

The protecting effect was shown with a dose at least equal (3.12 mg/kg/i.p.) to that of Vincamine taken as reference of activity (G. Perrault, M. Liutkus, R. Boulu and P. Rossignol-J. Pharmacol. (Paris) 1976, 7, (1), 27).

Table II also shows the results obtained by using the same method, but the administration of tested compounds was made orally and the test was effected an hour after administration.

TABLE II

| | Hypobar hypoxemia test 1st dose of significant protection | |
|---|---|---|
| Compound tested | Intraperitoneal injection (mg/kg) | Orally (mg/kg) |

Table 1

| Code No. | Ar | R | Empirical formula | Molecular weight | Melting point (° C) | Yield (%) | Elementary analysis | | |
|---|---|---|---|---|---|---|---|---|---|
| | | | | | | | | C | H | N |
| 72 778 | 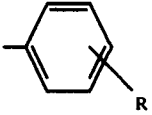 | 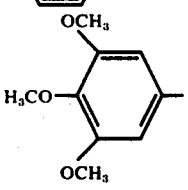 | $C_{20}H_{18}FN_3O_2$ | 351.38 | 168 | 82 | Calculated (%) Found (%) | 68.36 68.37 | 5.16 5.13 | 11.98 12.06 |
| 71 510 | 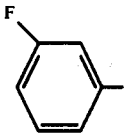 | 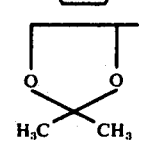 | | | | | | | | |
| | | 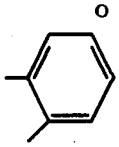 | $C_{27}H_{31}N_3O_7$ | 509.54 | 118 | 56 | Calculated (%) Found (%) | 63.64 64.84 | 6.13 6.02 | 8.25 8.34 |

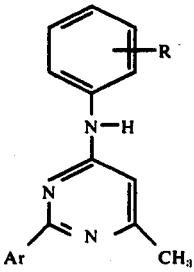

The derivatives of formula (I) were tested on laboratory animals and showed anti-anoxine properties according to the hypobar hypoxemia test described by Lauressergues et al (Therapie 26, 741, 1971).

The derivatives of formula (I) were administered by intraperitoneal injection to batches of 10 male mice (T.O.P.S.-C.R.F.), 30 minutes before being placed in a glass desiccator where a barometric pressure of 190 mm Hg was created in 30 seconds. The survival time of the mice is estimated by the stopping of respiration. The significance of the effect in relation to that of non-treated type samples is calculated on the threshold P = 0.05 by the test t.

| Derivatives of the invention | | |
|---|---|---|
| 72 778 | 1.56 | inactive at 25 |
| 71 510 | 3.12 | inactive at 25 |
| Reference compound | | |
| Vincamine | 3.12 | 25 |

As can be seen from a comparison between the pharmacologically active doses mentioned above and the lethal doses given below, the divergence between the doses is sufficient to permit the use of the derivatives of formula (I) in therapeutics.

The derivatives of formula I have been tested on animals in the laboratory and have been shown to possess sedative, antiinflammatory and antiulcerous properties.

1. Sedative properties

The derivatives of formula I, administered by oral means to the mouse, reduce the number of explorations in the escape enclosure and in an actimeter having luminous beams and photoelectric cells.

By way of example, the following Table III lists the percentage diminution in the number of explorations in the escape enclosure, resulting from the administration of 100mg/kg/p.o. of different derivatives of formula I.

TABLE III

| Code No. of derivatives tested | Percentage diminution of number of explorations (%) |
| --- | --- |
| 71 510 | 40 |
| 72 778 | 35 |

2. Antiulcerous properties

The derivatives of formula I, administered by oral means, reduce the extent of gastric ulcers provoked in a rat by tying of the pylorus (Shay ulcers).

Administration of 50mg/kg/i.p. of Code No. 71 510 caused a 35% reduction of Shay ulcers.

3. Antiinflammatory properties

These properties are shown by a diminution of the local oedema caused by the sub-plantar injection of a phlogogenic agent, such as carraghenine, in the rat following the oral administration of derivatives of formula I.

Administration of 100mg/kg/p.o. of Code No. 71 510 reduced sub-plantar oedema by 40%.

TABLE IV

| | TOXICITY | |
| Code No. of derivative tested | Dose administered to the mouse (mg/kg/p.o.) | Percentage Mortality (%) |
| --- | --- | --- |
| 71 510 | 2 000 | 0 |
| 72 778 | 2 000 | 0 |

The derivatives of formula (I) are useful in the treatment of gastro-duodenal ulcers, oedemas, anxiety, nervousness and diverse originating pains.

They may be administered by oral means, in the form of tablets, gelules and dragees, containing 25 to 400 mg of active ingredient (1 to 6 times per day), or suspensions containing 0.2 to 5% of active ingredient (10 to 100 drops, 1 to 3 times per day), by parenteral means in the form of injectable ampoules containing 10 to 150 mg of active ingredient (1 to 3 times per day) and by rectal means in the form of suppositories containing 25 to 300 mg of active ingredient (1 to 3 time per day).

The derivatives of formula (I) are prescribed in the treatment of cerebral deficiencies connected with an insufficiency of tissue oxygenation.

They will be administered orally in the form of pills, tablets and gelules containing 50 to 500 mg of the active ingredient (2 to 6 per day), in the form of a solution containing 0.5 to 5% of the active ingredient (20 to 60 drops - 2 to 6 times per day) and by parenteral injection in the form of injectable phials containing 50 to 500 mg of the active ingredient (1 to 3 per day).

Accordingly the present invention also relates to a therapeutic composition comprising a derivative of the general formula (I) together with a therapeutically acceptable carrier.

The embodiments of the invention in which an exclusive property or privilege is claimed are defined as follows:

1. A compound having the formula

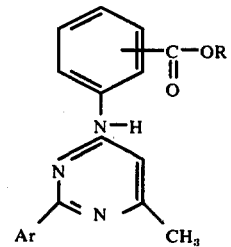

in which
Ar is m-fluorophenyl and R is ethyl, or
Ar is 3,4,5-trimethoxyphenyl and R is 2,2-dimethyl-1,3-dioxolan-4-yl methyl.

2. A compound as claimed in claim 1 in which Ar is m-fluorophenyl and R is ethyl.

3. A compound as claimed in claim 1 in which Ar is 3,4,5-trimethoxyphenyl and R is 2,2-dimethyl-13,-dioxolan-4-yl methyl.

* * * * *